(12) United States Patent
Beardsley

(10) Patent No.: US 8,197,446 B2
(45) Date of Patent: Jun. 12, 2012

(54) ACCESS CANNULA WITH HINGE RESTRICTOR

(75) Inventor: John W. Beardsley, Hamden, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 74 days.

(21) Appl. No.: 12/468,271

(22) Filed: May 19, 2009

(65) Prior Publication Data

US 2009/0326460 A1 Dec. 31, 2009

Related U.S. Application Data

(60) Provisional application No. 61/075,524, filed on Jun. 25, 2008.

(51) Int. Cl.
*A61M 39/04* (2006.01)

(52) U.S. Cl. ......... 604/167.03; 604/167.01; 604/164.01; 604/164.02

(58) Field of Classification Search ............. 604/167.01, 604/167.03, 167.06, 164.01, 164.02
See application file for complete search history.

(56) References Cited

U.S. PATENT DOCUMENTS

| | | | |
|---|---|---|---|
| 4,795,426 A | 1/1989 | Jones | |
| 4,943,280 A | 7/1990 | Lander | |
| 5,127,909 A | 7/1992 | Shichman | |
| 5,180,373 A | 1/1993 | Green et al. | |
| 5,209,737 A | 5/1993 | Ritchart et al. | |
| 5,342,315 A | 8/1994 | Rowe et al. | |
| 5,360,417 A | 11/1994 | Gravener et al. | |
| 5,389,081 A | 2/1995 | Castro | |
| 5,397,314 A | 3/1995 | Farley et al. | |
| 5,407,433 A | 4/1995 | Loomas | |
| 5,484,418 A | 1/1996 | Quiachon et al. | |
| 5,492,304 A | 2/1996 | Smith et al. | |
| 5,549,565 A | 8/1996 | Ryan et al. | |
| 5,603,702 A | 2/1997 | Smith et al. | |
| 5,634,908 A | 6/1997 | Loomas | |
| 5,657,963 A | 8/1997 | Hinchliffe et al. | |
| 5,685,854 A | 11/1997 | Green et al. | |
| 5,720,759 A | 2/1998 | Green et al. | |
| 5,722,958 A | 3/1998 | Gravener et al. | |
| 5,727,770 A | 3/1998 | Dennis | |
| 5,752,970 A * | 5/1998 | Yoon | 606/185 |
| 5,797,888 A * | 8/1998 | Yoon | 604/530 |
| 5,820,600 A | 10/1998 | Carlson et al. | |
| 5,865,807 A * | 2/1999 | Blake, III | 604/167.06 |

(Continued)

FOREIGN PATENT DOCUMENTS

EP 1702575 9/2006

(Continued)

OTHER PUBLICATIONS

European Search Report, Application No. EP 09251622, dated Oct. 23, 2009.

*Primary Examiner* — Laura Bouchelle

(57) ABSTRACT

A cannula assembly adapted to facilitate the percutaneous introduction of surgical instrumentation. In particular, the cannula assembly includes a cannula housing and a cannula member incorporating an restrictor hinge. The restrictor hinge is configured and dimensioned to transition from a first, initial stage in which an initial internal dimension is defined, to a second, expanded stage, such that the proper orientation of any surgical instrument inserted into the cannula may be achieved and a substantially fluid-tight seal may be formed therewith.

14 Claims, 10 Drawing Sheets

U.S. PATENT DOCUMENTS

| | | |
|---|---|---|
| 5,895,377 A | 4/1999 | Smith et al. |
| 6,228,061 B1 | 5/2001 | Flatland et al. |
| 6,383,160 B1 | 5/2002 | Madsen |
| 6,458,103 B1 | 10/2002 | Albert et al. |
| 7,025,747 B2 | 4/2006 | Smith |
| 7,063,685 B2 | 6/2006 | Rome |
| 2002/0072713 A1 | 6/2002 | Almond et al. |
| 2003/0187397 A1 | 10/2003 | Vitali |
| 2004/0064100 A1 | 4/2004 | Smith |
| 2004/0082969 A1 | 4/2004 | Kerr |
| 2005/0165281 A1 | 7/2005 | Ravikumar et al. |
| 2005/0277946 A1* | 12/2005 | Greenhalgh .................. 606/108 |
| 2006/0020281 A1 | 1/2006 | Smith |
| 2006/0047284 A1 | 3/2006 | Gresham |
| 2008/0091144 A1 | 4/2008 | Moran et al. |
| 2008/0097332 A1* | 4/2008 | Greenhalgh et al. ...... 604/167.06 |

FOREIGN PATENT DOCUMENTS

| | | |
|---|---|---|
| WO | 0152754 | 7/2001 |

* cited by examiner

ACCESS CANNULA WITH HINGE RESTRICTOR

CROSS REFERENCE TO RELATED APPLICATION

The present application claims the benefit of and priority to U.S. Provisional Application Ser. No. 61/075,524 filed on Jun. 25, 2008, the entire contents of which are incorporated herein by reference.

BACKGROUND

1. Technical Field

The present disclosure relates to cannula assemblies which permit the introduction of surgical instrumentation to the internal cavities of a patient. In particular, the present disclosure relates to cannula assemblies adapted for the internal receipt of surgical instruments varying in size.

2. Background of the Related Art

Minimally invasive procedures are continually increasing in number and variation. Forming a temporary pathway with a relatively small diameter to a surgical site is one feature of most minimally invasive surgical procedures. The most common method of providing such a pathway is by inserting a obturator assembly through the skin vis-à-vis a cannula assembly generally formed of a cannula member or sleeve attached to a cannula housing. In many procedures the obturator is inserted into the insufflated body cavity of a patient. In such procedures, the cannula assembly may incorporate seal mechanisms or assemblies that are utilized to provide the necessary pathway to the surgical site while maintaining a fluid-tight seal, both with and without an instrument inserted therethrough, so as to minimize leakage of insufflation gases through the inserted cannula. A particularly suitable valve assembly is disclosed in commonly-assigned, copending U.S. Pat. No. 5,603,702 to Smith et al., which issued Feb. 18, 1997, the entire contents of which are hereby incorporated by reference.

A limitation of known cannula assemblies concerns the dimensions of the cannula member. Often times, during a single procedure, a clinician will need to employ various surgical implements that may vary in size. Accordingly, there is a need in the art for a cannula that can accommodate instrumentation of different sizes.

SUMMARY

The present disclosure is directed to a cannula assembly that facilitates percutaneous access to a patient's internal cavities. The cannula assembly disclosed herein is adapted to accommodate instrumentation of different sizes. In one embodiment, the cannula assembly includes a housing and a cannula member extending from the housing and defining a longitudinal axis. The cannula member includes an outer wall portion and a restrictor hinge portion. The restrictor hinge portion has at least one restrictor hinge extending radially inward from the outer wall portion. The restrictor hinge is adapted to transition from a first stage in which the restrictor hinge defines a first internal dimension to a second stage in which the restrictor hinge defines a second internal dimension upon engagement with a surgical instrument inserted through the cannula member. The second internal dimension of the restrictor hinge is greater than the first internal dimension. The at least one restrictor hinge is dimensioned and configured to normally bias the surgical instrument into a position in general alignment with the longitudinal axis of the cannula member. The restrictor hinge portion may include a plurality of restrictor hinges. The plurality of restrictor hinges may be concentrically arranged about the longitudinal axis and dimensioned and configured to normally bias the object into a position in general alignment with the longitudinal axis of the cannula member.

In one embodiment, the restrictor hinge portion includes a sealing member. The sealing member is adapted to establish a sealing relation with the surgical instrument. The restrictor hinge portion may include an elastomeric jacket. The elastomer jacket is adapted to establish a sealing relation with the surgical instrument.

The restrictor hinge portion may be monolithically formed with the outer wall portion. The at least one restrictor hinge may include two hinge elements. The at least one restrictor hinge may define a general sinusoidal profile. The at least one restrictor hinge may define a general arcuate profile.

The cannula member defines an axial length. The axial length remains substantially constant upon transition of the restrictor hinge portion between the first stage and the second stage.

These and other features of the cannula assembly will become more readily apparent to those skilled in the art from the following detailed description of preferred embodiments of the present disclosure.

BRIEF DESCRIPTION OF THE DRAWINGS

Preferred embodiments of the present disclosure are described hereinbelow with references to the drawings, wherein.

DETAILED DESCRIPTION OF THE EMBODIMENTS

Figure 1:
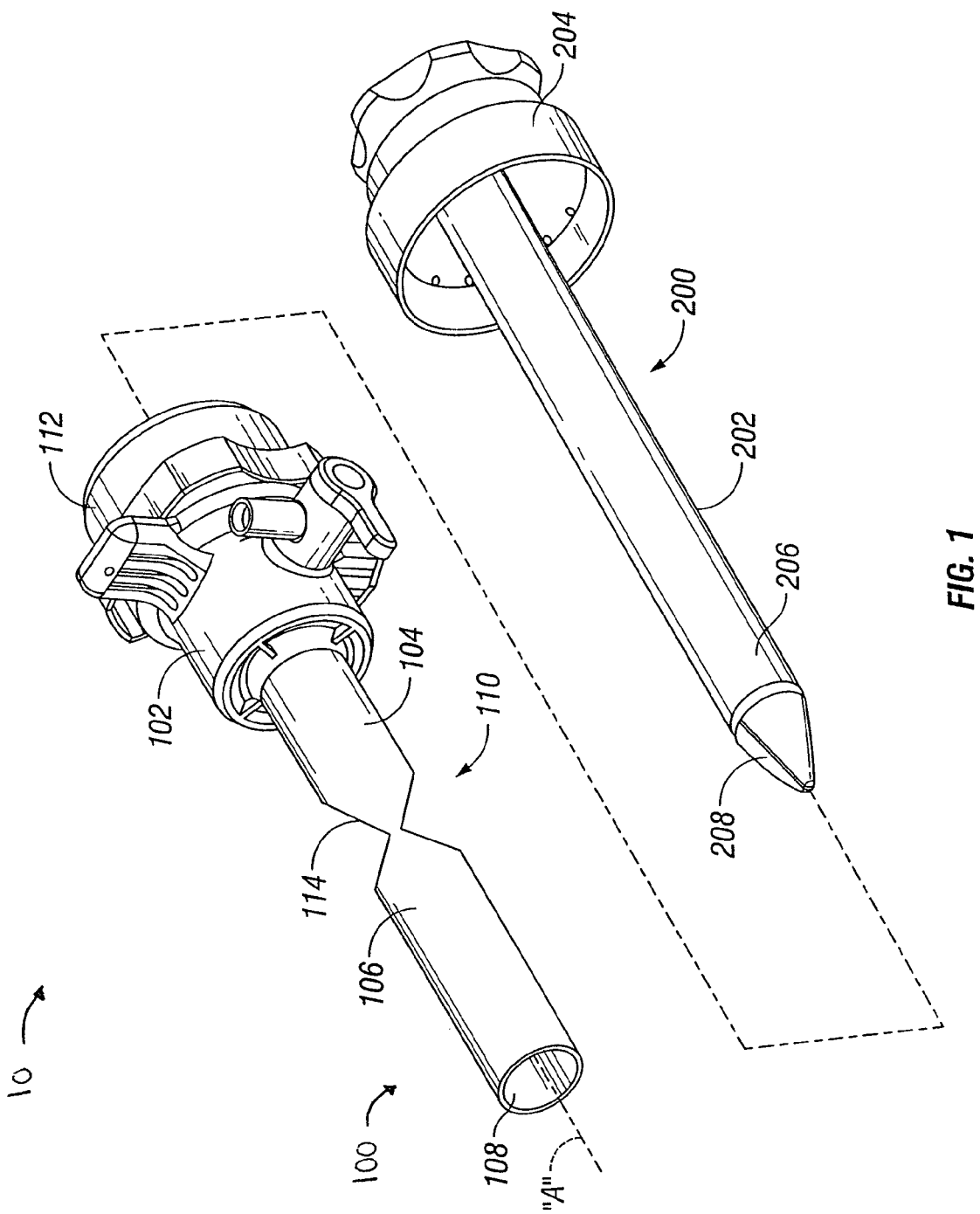
FIG. 1 is a perspective view of a surgical system in accordance with the principles of the present disclosure illustrating a cannula assembly incorporating an restrictor hinge portion and an obturator assembly.

In the drawings and in the description which follows, the term proximal", as is traditional, will refer to the end of the apparatus which is closest to the clinician, while the term "distal" will refer to the end which is furthest from the clinician.

The present disclosure contemplates the introduction into a body cavity of all types of surgical instruments including clip appliers, graspers, dissectors, retractors, staplers, laser fibers, photographic devices, endoscopes and laparoscopes, tubes, and the like. All such objects are referred to herein as "instrument(s)".

Referring now in detail to the drawing figures, in which like references numerals identify similar or identical elements, there is illustrated, in FIG. 1, a surgical system in accordance with the present disclosure. System 10 has particular application in laparoscopic procedures with respect to accessing the abdominal cavity, and the like, and may be used in any such surgical procedure where the peritoneal cavity is insufflated with a suitable gas, e.g., $CO_2$, to separate the cavity wall from the internal organs housed therein. System 10 includes cannula assembly 100 and obturator assembly 200, which is positionable therein.

Obturator assembly 200 includes obturator 202, which includes obturator housing 204 and sleeve or outer member 206 extending therefrom. Obturator housing 204 is advantageously dimensioned for grasping by a clinician. Obturator 202 further includes penetrating end 208 which serves to puncture the abdominal cavity or the like, thereby creating an access point through which at least a portion of a surgical procedure may be conducted. Following penetration, obturator assembly 200 is removed from cannula assembly 100 to permit the subsequent introduction of surgical instrumentation utilized to carry out the remainder of the procedure through cannula assembly 100.

Referring still to FIG. 1, cannula assembly 100 will be discussed. In one embodiment, cannula assembly 100 includes cannula housing 102 and cannula member 104 having an outer wall portion 106 and defining longitudinal axis "A". Cannula member 104 defines an internal longitudinal lumen 108 dimensioned to permit the passage of surgical instrumentation therethrough. Cannula member 104 extends distally from cannula housing 102 and includes an restrictor hinge portion 110. Either or both of cannula housing 102 and cannula member 104 may be opaque or transparent, either wholly or in part, and may be fabricated from any biocompatible material including metals or polymers.

The present disclosure contemplates that cannula assembly 100 may include an internal seal or valve (not shown), such as a duck-bill valve or other zero closure valve, adapted to close in the absence of a surgical instrument to prevent passage of insufflation gases through the cannula assembly 100, as is known in the art. An example of such an internal seal or valve is disclosed in commonly assigned U.S. Pat. No. 5,820,600 to Carlson, et. al., which issued Oct. 13, 1998, the disclosure of which is incorporated by reference herein. Alternatively, it is contemplated that cannula assembly 100 may include a seal assembly 112 that may be releasably mounted to cannula housing 102. Means for releasably connecting seal assembly 112 to cannula housing 102 may include a bayonet coupling, threaded connection, latch, friction fit, tongue and groove arrangements, snap-fit, etc. Seal assembly 112 includes at least one internal seal or valve (not shown) adapted to form a fluid tight seal about an instrument inserted therethrough, as is known in the art. An example of one such suitable seal is the fabric seal disclosed in commonly assigned U.S. Pat. No. 6,702,787 to Racenet et al. (hereinafter "Racenet"), which issued Mar. 9, 2004, the entire contents of which are incorporated herein by reference. The seal disclosed in the Racenet patent may be a flat septum seal having a first layer of resilient material and a second fabric layer juxtaposed relative to the first layer. Further details of the seal may be ascertained by reference to Racenet. In the alternative, the seal assembly 112 may comprise an integral part of the cannula assembly 100.

Referring now to FIGS. 2-4B, restrictor hinge portion 110 will be discussed. Restrictor hinge portion 110 includes restrictor hinge 114, which provides for a flex point such that the internal dimension of cannula member 104 may be enlarged to accommodate the insertion of surgical instrumentation of varying diameters therethrough. Restrictor hinge 114 may be circumferentially or concentrically disposed about the longitudinal axis of cannula member 104, and is oriented in a pre-determined location along the length of cannula member 104. Restrictor hinge 114 may be formed of any resilient biocompatible material that may be substantially rigid, or substantially non-rigid in character.

Figure 2:
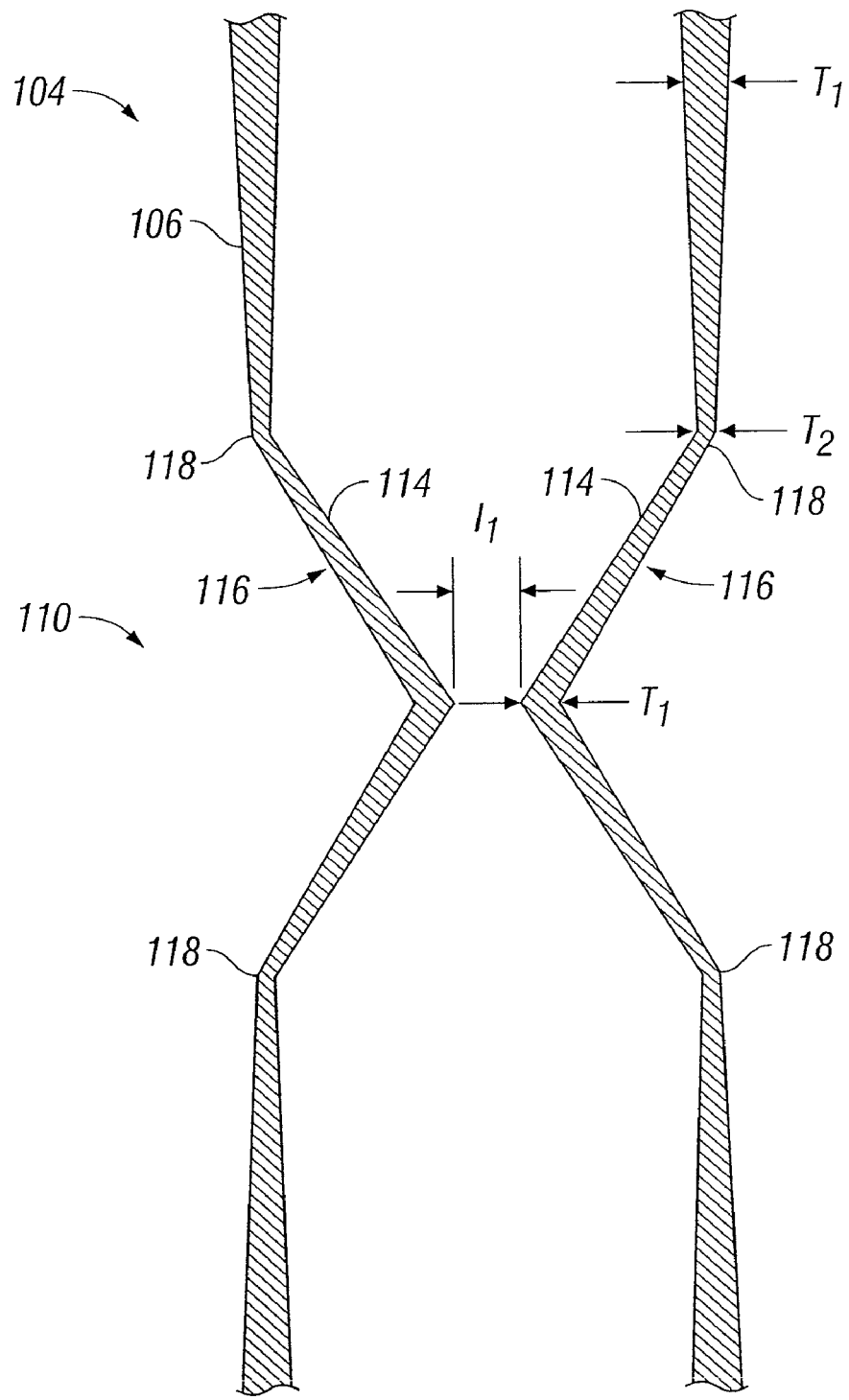
FIG. 2 is a cross-sectional view of the restrictor hinge portion of FIG. 1.

FIG. 2 depicts one embodiment of the restrictor hinge of the present disclosure. In this embodiment, restrictor hinge 114 includes hinge elements 116, which are attached to cannula member 104 at hinge points 118. In one embodiment, it is contemplated that the restrictor hinge, or plurality of hinges, as disclosed below, may be monolithically formed with outer wall portion 106. In this embodiment, cannula member 104 defines a wall thickness T1 which may begin to taper, thereby defining a second wall thickness T2 at the location where hinge points 118 are formed. At hinge points 118, wall thickness T2 is appreciably less than that at T1 such that hinge elements 116 may be allowed to flex inwardly about hinge points 118, thereby allowing for the insertion of surgical instruments. In each of the embodiments that follow, the present disclosure contemplates that the walls of the cannula member may taper at the location where the hinge points are formed, thereby allowing the hinge restrictor hinge to flex upon the insertion of a surgical instrument.

It is contemplated that the cannula member and the restrictor hinge may be die cast from suitable metals or molded from suitable plastics or polymers. One skilled in the art, however, will realize that other materials and fabrication methods suitable for assembly and manufacture, in accordance with the present disclosure, would also be appropriate.

Figure 3A:
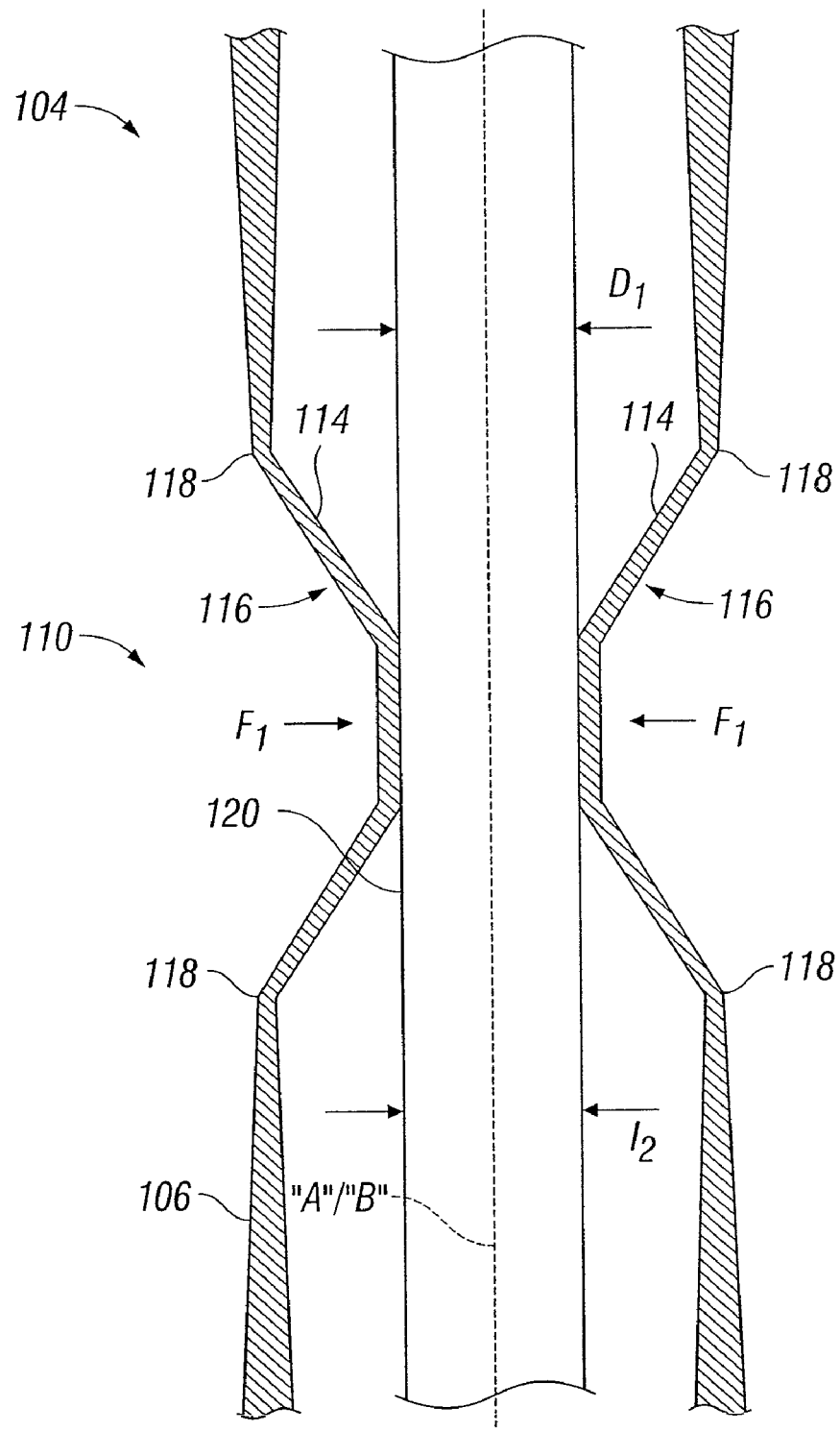
FIG. 3A is a cross-sectional view of one embodiment of the restrictor hinge in accordance with the principles of the present disclosure with a first surgical instrument inserted therethrough.

Restrictor hinge 114 is adapted to transition from a first, initial, or un-activated, stage or condition in which there is no surgical instrument inserted therethrough, as seen in FIG. 2, to a second, expanded, or activated, stage or condition in which restrictor hinge 114 accommodates the insertion of an instrument therethrough, as seen in FIG. 3A. In its first stage, restrictor hinge 114 defines a first internal dimension $I_1$. Upon the introduction of first instrument 120, restrictor hinge 114 transitions to its second stage, defining a second internal dimension $I_2$ and applying a force $F_1$ to first instrument 120 inserted therethrough.

It is contemplated that, in the second stage, the second internal dimension $I_2$ defined by restrictor hinge 114 may be in the range of about 5 mm to about 12 mm, or about 3 mm to about 15 mm, or larger, dependent upon the procedure in which it is employed and the corresponding size of the instrument to inserted therein.

Figure 3B:
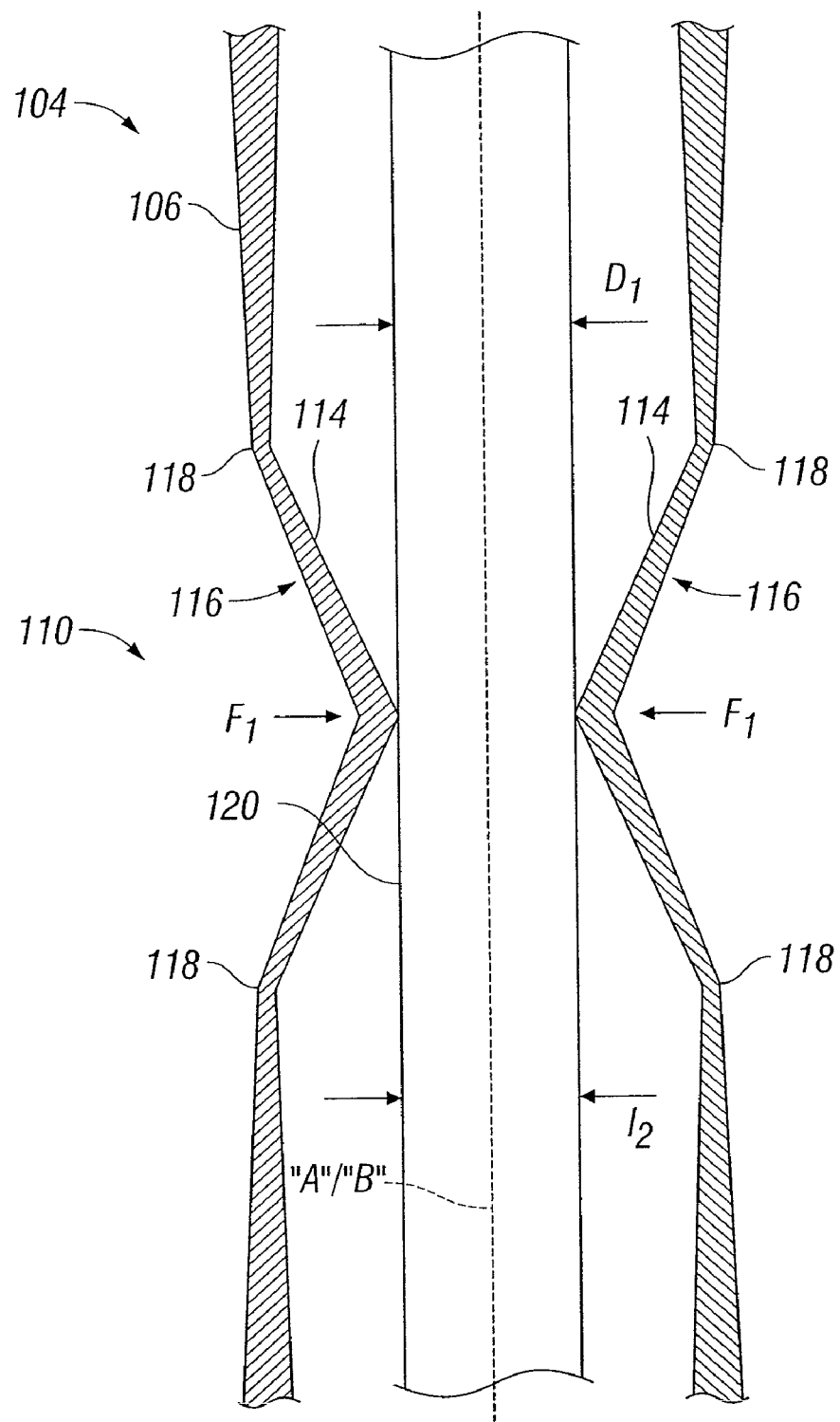
FIG. 3B is a cross-sectional view of another embodiment of the restrictor hinge in accordance with the principles of the present disclosure with a first surgical instrument inserted therethrough.

As seen in FIG. 3A, first instrument 120 defines longitudinal axis "B" and first diameter $D_1$. In its activated stage, restrictor hinge 114 applies a force F1 to first instrument 120 such that a substantially fluid tight seal is created between restrictor hinge 114 and the surface of the instrument, thereby substantially inhibiting the escape of any insufflation gases. As seen in FIG. 3A, the present disclosure contemplates that restrictor hinge 114 may substantially deform such a flat contact surface is created with the first surgical instrument. The present disclosure also contemplates, however, that restrictor hinge 114 may not substantially deform, as seen in FIG. 3B. As discussed above, force F1 also maintains the desired orientation of first instrument 120. While FIGS. 3A-3B depict the longitudinal axes "A" and "B" of cannula member 104 and first instrument 120, respectively, as substantially collinear, the present disclosure contemplates that restrictor hinge 114 may orient first instrument 120 within cannula member 104 such that axes "A" and "B" are merely substantially parallel. In its activated condition, restrictor hinge 114 defines a second internal dimension $I_2$ that is substantially equivalent to the first diameter $D_1$ of first instrument 120.

Figure 4A:
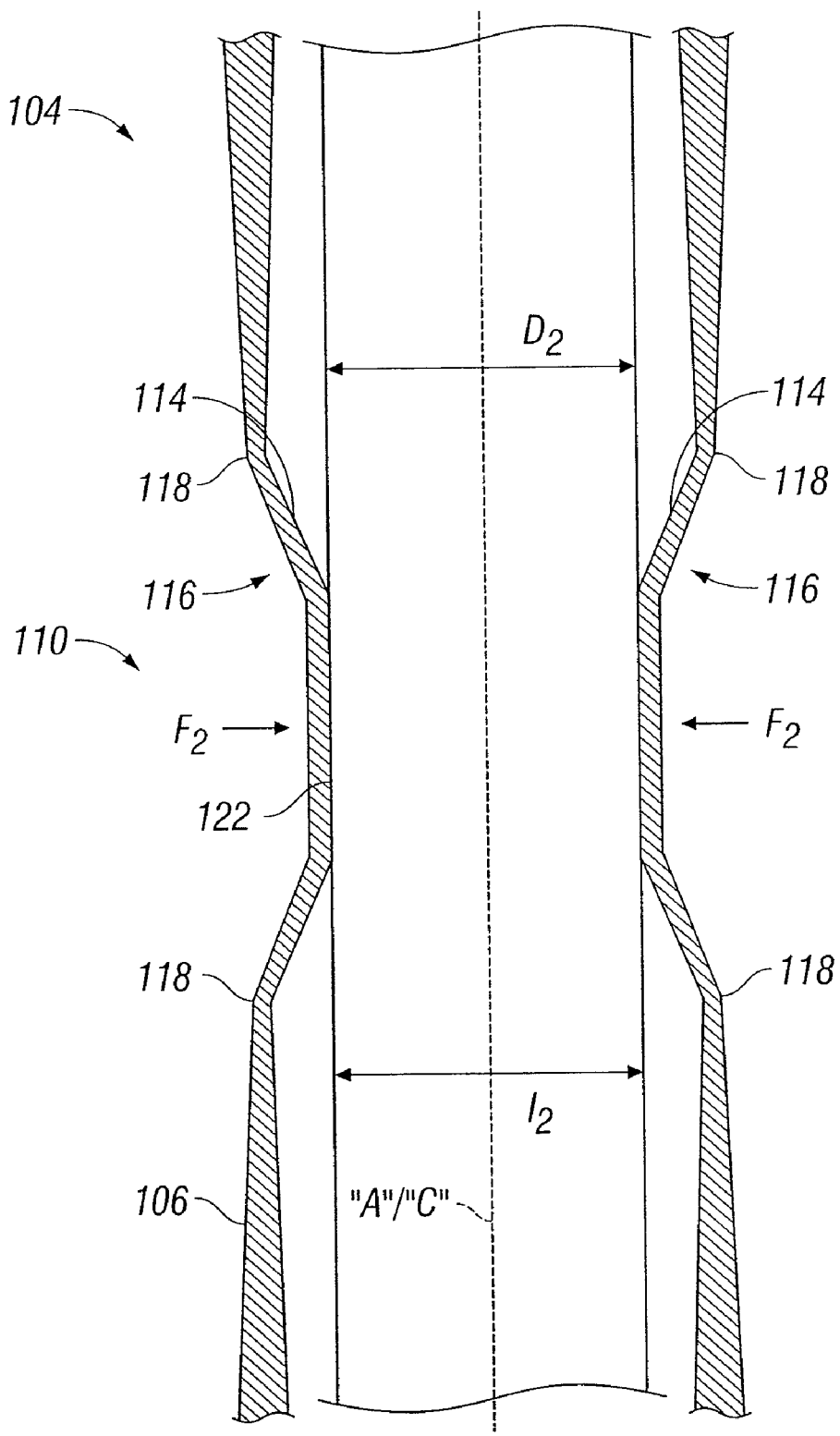
FIG. 4A is a cross-sectional view of one embodiment of the restrictor hinge in accordance with the principles of the present disclosure with a second surgical instrument inserted therethrough.
Figure 4B:
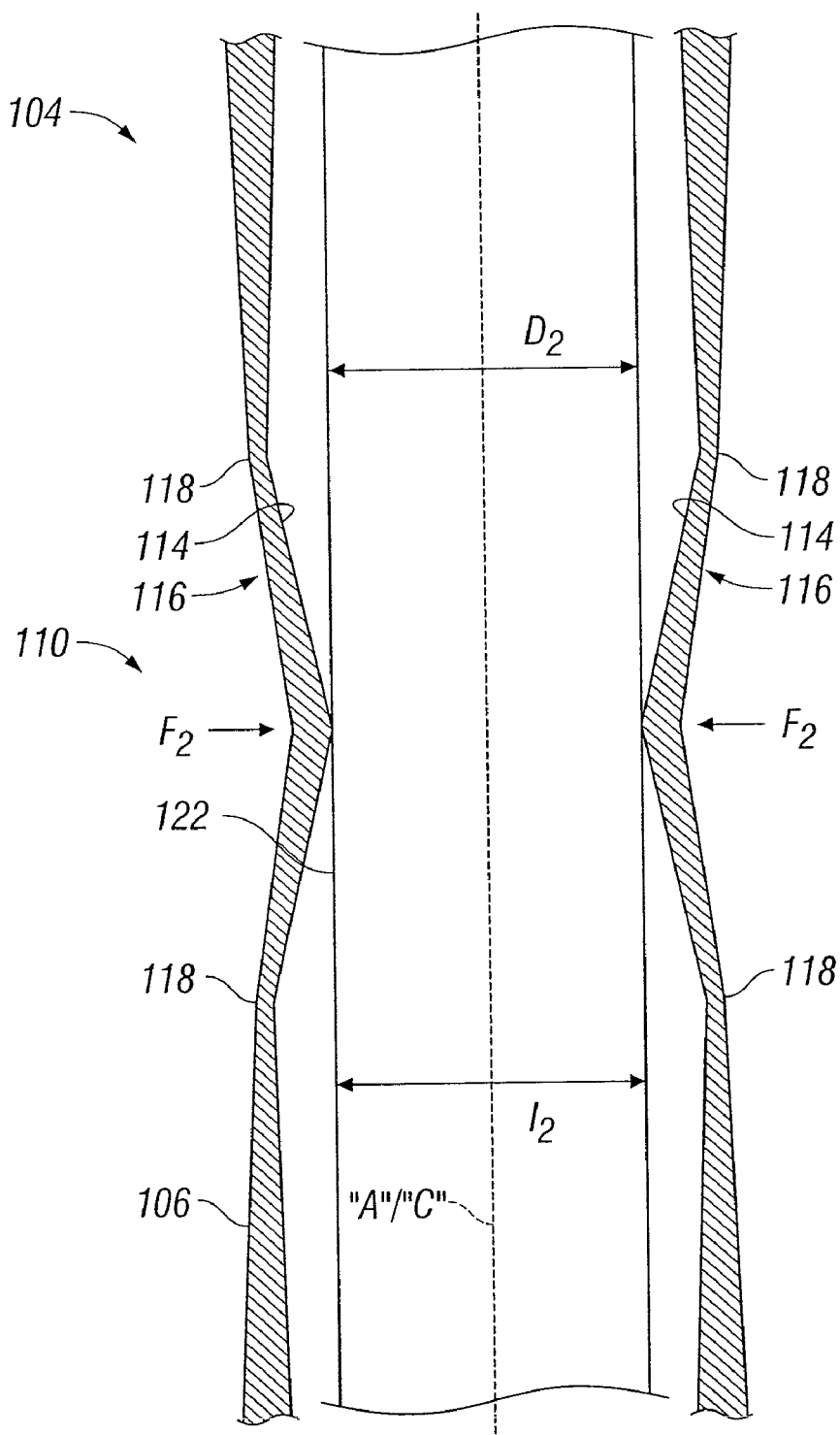
FIG. 4B is a cross-sectional view of another embodiment of the restrictor hinge in accordance with the principles of the present disclosure with a second surgical instrument inserted therethrough.

As suggested above, restrictor hinge 114 allows the cannula assembly disclosed herein to accommodate surgical instruments of various sizes. FIGS. 4A-4B also depict restrictor hinge 114 in the activated condition, but with a second instrument 122 that defines a second longitudinal axis "C" and second diameter $D_2$, which is larger than first diameter $D_1$ of first instrument 120, inserted therethrough. As seen in FIGS. 4A-4B, in its activated condition, restrictor hinge 114 again applies a force F2 to second instrument 122 such that a substantially fluid tight seal is created between restrictor hinge 114 and the surface of the instrument. As seen in FIG. 4A, the present disclosure contemplates that restrictor hinge 114 may substantially deform such a flat contact surface is created with the second surgical instrument. The present disclosure also contemplates, however, that restrictor hinge 114 may not substantially deform, as seen in FIG. 4B. Force F2 also serves to maintain the desired orientation of second instrument 122. As discussed above with respect to FIGS. 3A-3B, while FIGS. 4A-4B depict the longitudinal axes "A" and "C" of cannula member 104 and second instrument 122, respectively, as substantially collinear, the present disclosure contemplates that restrictor hinge 114 may orient second instrument 122 within cannula member 104 such that axes "A" and "C" are merely substantially parallel. In its activated condition, restrictor hinge 114 now defines a second internal dimension $I_2$ that is substantially equivalent to the second diameter $D_2$ of second instrument 122.

While the internal dimensions of the cannula member will change to accommodate the surgical instrument inserted therethrough, the present disclosure contemplates that the overall axial dimension of the cannula member will remain constant.

Figure 5B:
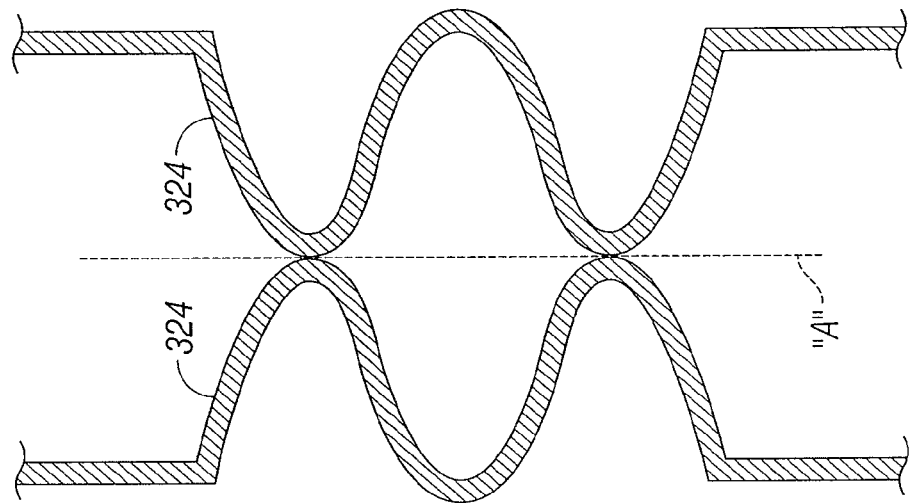
FIG. 5B is a cross-sectional view of one embodiment of the restrictor hinge in accordance with the principles of the present disclosure having a generally sinusoidal profile.
Figure 5A:
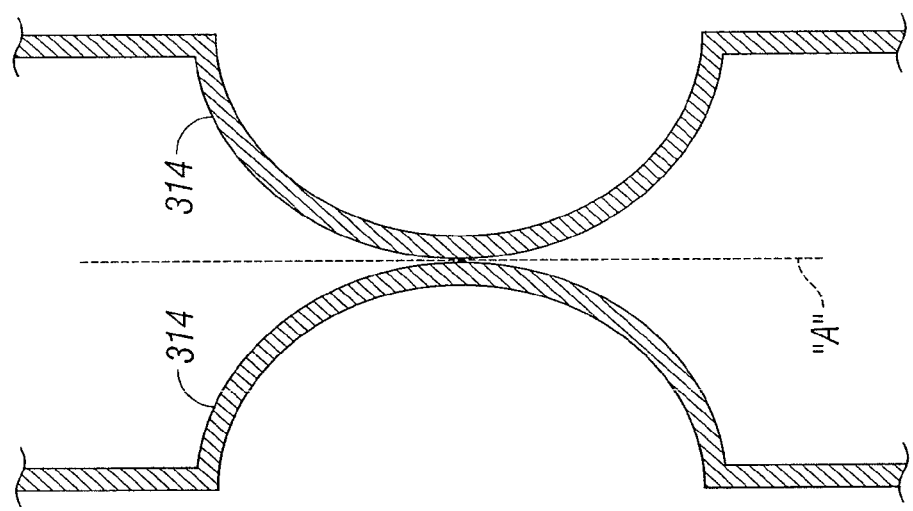
FIG. 5A is a cross-sectional view of one embodiment of the restrictor hinge in accordance with the principles of the present disclosure having a generally arcuate profile.

In one embodiment of the present disclosure, it is contemplated that restrictor hinge 314 may have an arcuate profile, as depicted in FIG. 5A. In another embodiment, it is contemplated that restrictor hinge 324 may have a sinusoidal profile, as depicted in FIG. 5B.

Figure 6B:
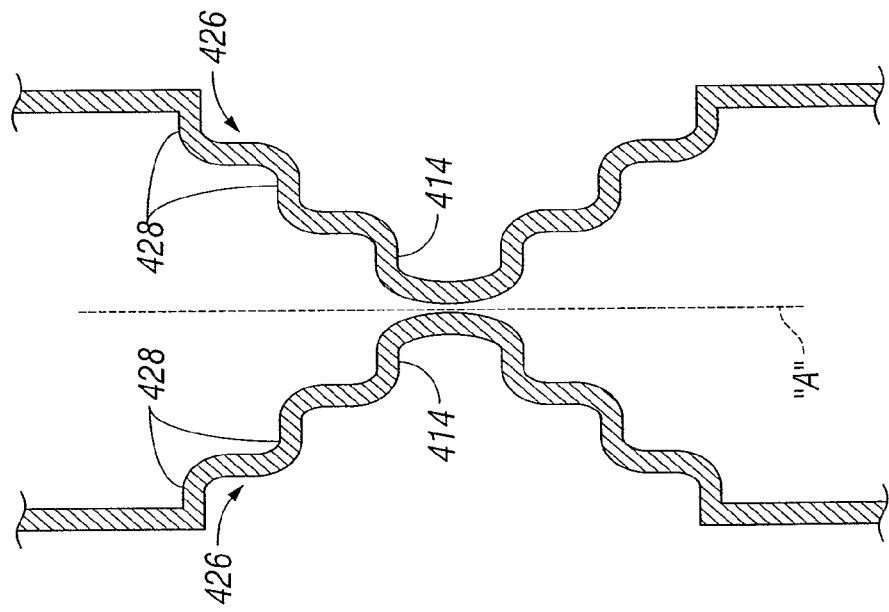
FIGS. 6A-6B are cross-sectional views of alternate embodiments of the restrictor hinge in accordance with the principles of the present disclosure incorporating multiple hinge elements.
Figure 6A:
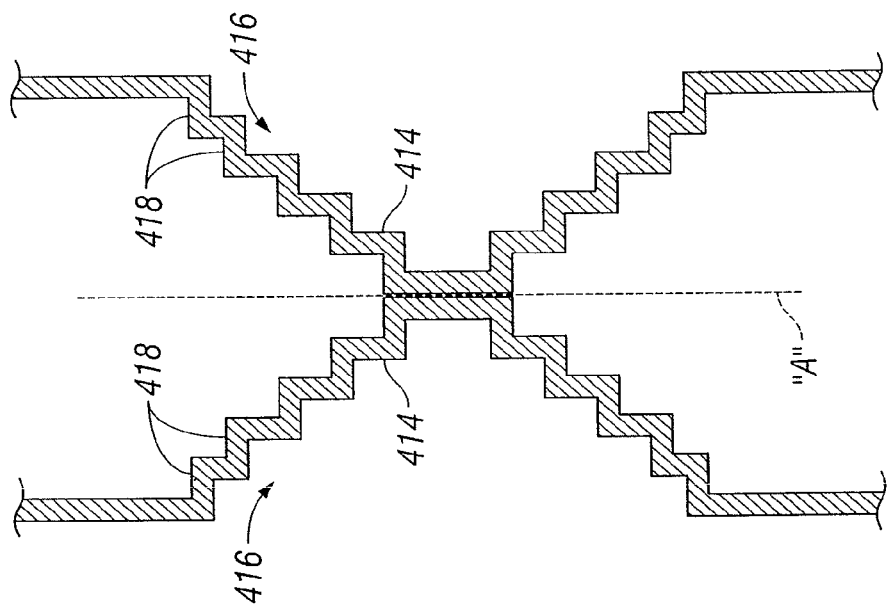

As seen in FIGS. 6A-6B, in additional embodiments, it is contemplated that restrictor hinge 414 may incorporate hinge elements 416 that include multiple hinge members 418. In another embodiment, it is contemplated that hinge elements 426 may include multiple hinge members 428 that exhibit a substantially sinusoidal profile, as described above with respect to the embodiment depicted in FIG. 5A. In the multiple hinge member embodiments, hinge elements 416 and 426 may also be concentrically or circumferentially arranged about the longitudinal axis of the cannula member, as described above.

Figure 7B:
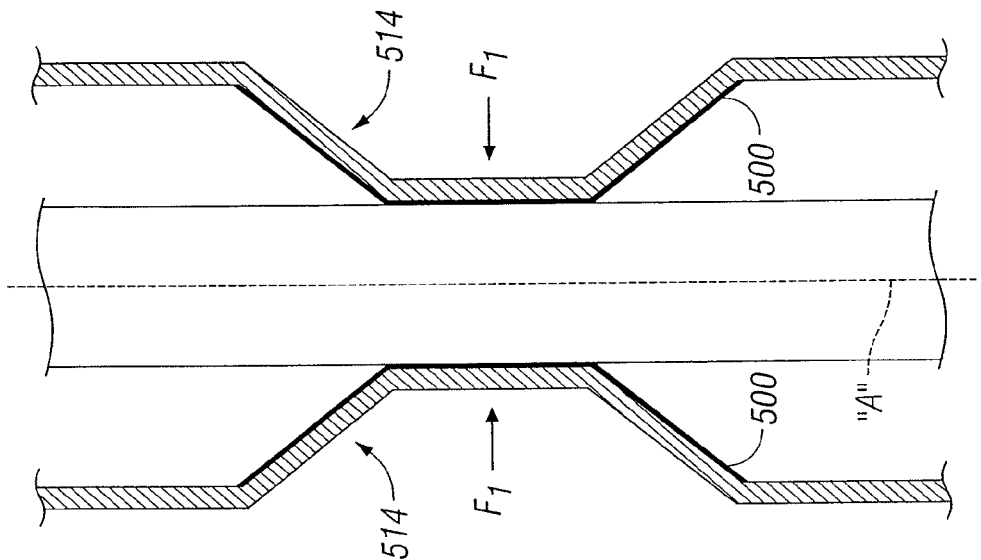
FIG. 7B is a cross-sectional view of the embodiment of FIG. 7A with a surgical instrument inserted through the restrictor hinge.
Figure 7A:
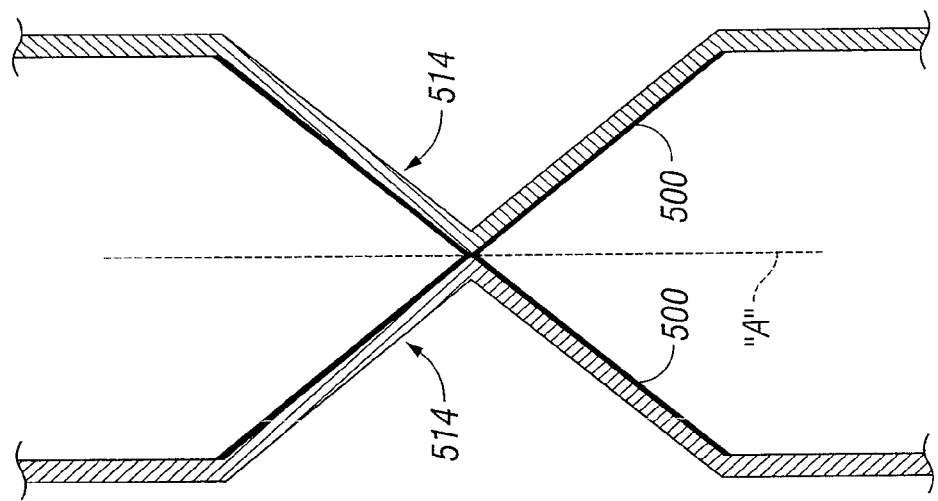
FIG. 7A is a cross-sectional view of one embodiment of the present disclosure incorporating a restrictor hinge with a sealing member.
Figure 8:
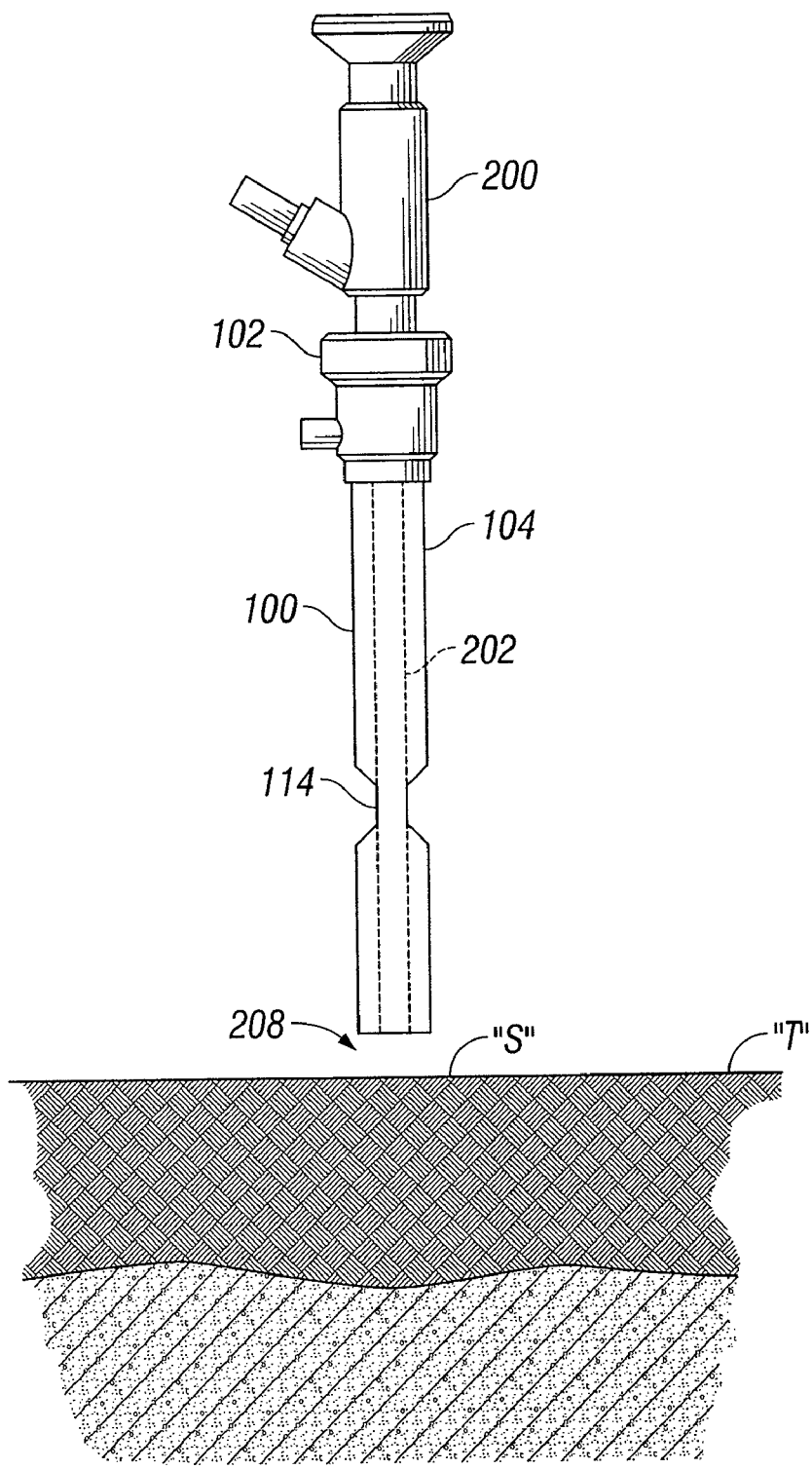
FIG. 8 is a perspective view illustrating the obturator assembly mounted to the cannula assembly to permit the penetration of tissue.

In one embodiment, the present disclosure contemplates that restrictor hinge 514 may include a sealing member 500, as seen in FIG. 7A. In this embodiment, the sealing member 500 expands as instrument I is passed therethrough, as seen in FIG. 7B, thereby enhancing the substantially fluid-tight seal created between restrictor hinge 514 and instrument I. Sealing member 500 may include an elastomeric coating or an elastomeric jacket. Examples of elastomeric coatings include thermoplastic elastomers, thermoplastic rubbers, urethanes, latex, and silicone.

Referring now to FIGS. 1, 2, 3A-3B, and 8, the use and function of the system 10 will be discussed. The peritoneal cavity is first insufflated with a suitable biocompatible gas such as, e.g., $CO_2$ gas, such that the cavity wall is raised and lifted away from the internal organs and tissue housed therein, providing greater access thereto, as is known in the art. The insufflation may be performed with an insufflation needle or similar device. Following insufflation, obturator assembly 200 is positioned within cannula assembly 100, specifically, first through a seal assembly (not shown), if any, and then through cannula housing 102 and cannula member 104, respectively. Thereafter, obturator 202 is advanced such that contact is made between penetrating end 208 of obturator 202 and skin site "S" of tissue "T". A force is then applied to the proximal end of obturator assembly 200 such that penetrating end 208 may puncture tissue "T". Following penetration, obturator assembly 200 is removed from cannula assembly 100. Thereafter, a variety of surgical instrumentation may be inserted through cannula member 104 of cannula assembly 100 to carry out the remainder of the surgical procedure. As described above, upon insertion, a substantially fluid-tight seal will be created between restrictor hinge 114 and the surface of the instrument. Additionally, restrictor hinge 114 may maintain the desired orientation of the instrument and may align its axis with that of cannula member 104.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A cannula assembly, which comprises:
   a housing; and
   a cannula member having a proximal end secured to the housing, and a distal end, the cannula member defining a longitudinal axis and including an outer wall, wherein a portion of the outer wall spaced from the distal end of the cannula member forms a restrictor hinge extending radially inward towards the longitudinal axis so as to engage a surgical instrument inserted therethrough, the restrictor hinge including hinge segments obliquely arranged with respect to the longitudinal axis and intersecting at an inflection segment, the restrictor hinge being adapted to transition from a first stage, in which the inflection segment of the restrictor hinge defines a first internal dimension, to a second stage, in which the inflection segment of the restrictor hinge defines a second internal dimension, upon engagement of at least the inflection segment with the surgical instrument such that contact between the restrictor hinge and the surgical instrument is minimized, the second internal dimension being greater than the first internal dimension.

2. The cannula assembly according to claim 1, wherein the restrictor hinge is dimensioned, positioned, and configured to normally bias the surgical instrument into a position in general alignment with the longitudinal axis of the cannula member.

3. The cannula assembly according to claim 1, wherein the restrictor hinge includes an elastomeric jacket.

4. The cannula assembly according to claim 3, wherein the elastomeric jacket is adapted to establish a sealing relation with the surgical instrument.

5. The cannula assembly according to claim 1, wherein the restrictor hinge is monolithically formed with the outer wall.

6. The cannula assembly according to claim 1, wherein the cannula member defines an axial length, the axial length remaining substantially constant upon transitioning of the restrictor hinge between the first stage and the second stage.

7. The cannula assembly according to claim 1, wherein the inflection segment is dimensioned to extend along the entire perimeter of the outer wall.

8. The cannula assembly according to claim 1, including an individual sealing member mounted to an internal surface of the restrictor hinge, the sealing member being configured, dimensioned, and adapted to form a substantially fluid-tight seal with the surgical instrument upon insertion into the cannula member.

9. A cannula assembly, which comprises:
a housing; and
a cannula member extending from the housing along a longitudinal axis, the cannula member including an outer wall defining a longitudinal axis and having a longitudinal passage configured and dimensioned to removably receive a surgical instrument, the outer wall forming a restrictor hinge, the restrictor hinge being dimensioned and configured to transition from a first stage where the longitudinal passage is substantially closed to a second stage receiving the surgical instrument where contact between the restrictor hinge and the surgical instrument is minimized, the restrictor hinge configured, dimensioned, and positioned to normally bias the surgical instrument into general alignment with the longitudinal axis.

10. The cannula assembly according to claim 9, wherein the cannula member includes proximal and distal ends, the restrictor hinge being spaced from the distal end of the cannula member.

11. The cannula assembly according to claim 9, wherein the restrictor hinge is monolithically formed with the outer wall of the cannula member.

12. The cannula assembly according to claim 9, including an individual sealing member mounted to an internal surface of the restrictor hinge, the sealing member being configured, dimensioned, and adapted to form a substantially fluid-tight seal with the surgical instrument upon insertion into the cannula member.

13. The cannula assembly according to claim 9, wherein the restrictor hinge defines a general sinusoidal segment extending along the longitudinal axis.

14. The cannula assembly according to claim 9, where the restrictor hinge defines a general arcuate profile.

* * * * *